United States Patent
I

(10) Patent No.: US 6,708,345 B2
(45) Date of Patent: Mar. 23, 2004

(54) NECKTIE WEARING DEVICE

(76) Inventor: Chung-Lim I, 274-5 Sacheonjin-Ri, Sacheon-Myun, Gangneung, Gangwon-Do (KR), 210-853

( * ) Notice: Subject to any disclaimer, the term of this patent is extended or adjusted under 35 U.S.C. 154(b) by 0 days.

(21) Appl. No.: 10/384,612

(22) Filed: Mar. 11, 2003

(65) Prior Publication Data

US 2003/0213047 A1 Nov. 20, 2003

(30) Foreign Application Priority Data

May 17, 2002 (KR) .......................... 2002-15074

(51) Int. Cl.[7] ............................. A41D 25/04
(52) U.S. Cl. ............................. 2/145; 2/148
(58) Field of Search ..................... 2/144, 145–151, 2/152.1, 153, 154; 24/49.1, 66.1, 64, 50, 51

(56) References Cited

U.S. PATENT DOCUMENTS

| | | | | |
|---|---|---|---|---|
| 2,601,424 A | * | 6/1952 | Baker | 24/66.1 |
| 4,554,710 A | * | 11/1985 | Grant | 24/66.1 |
| 4,827,576 A | * | 5/1989 | Prince, Jr. | 24/66.1 |
| 4,835,821 A | * | 6/1989 | Durante | 24/66.1 |
| 4,972,523 A | * | 11/1990 | Begg | 2/145 |
| 5,864,882 A | * | 2/1999 | Kowalyk | 2/148 |
| 6,216,275 B1 | * | 4/2001 | Lee | 2/144 |

* cited by examiner

*Primary Examiner*—Tejash Patel
(74) *Attorney, Agent, or Firm*—G W i P S

(57) ABSTRACT

A necktie wearing device includes a support plate (1) having a curved shape corresponding to the front surface of a necktie knot, a magnet (3) mounted in the center of the support plate, a rod-shaped lifting plate (2) connected to the support plate by using strings (5) connected to both ends of the support plate, and a case (4) provided on one side of the support plate (1), which case has a magnet (3) therein. The device further includes a knot unit (7) made of a fiber and having a necktie knot shape, a space (8) being formed in the knot unit for insertion of the support plate (1), and a necktie drawing hole (9) being formed at the lower end of the knot unit. This necktie-wearing device enables a user to wear various kinds of neckties in an easier and more convenient way and allows a wearer to adjust the length of the necktie as desired.

2 Claims, 4 Drawing Sheets

NECKTIE WEARING DEVICE

BACKGROUND OF THE INVENTION

1. Field of the Invention

The present invention relates to a necktie-wearing device for helping to wear a necktie in an easier and more convenient way. Particularly, a new necktie-wearing device separately provides a knot and support plate inserted into the knot so as to allow for the wearing of various kinds of neckties in an easier and more convenient way and for adjusting the length of a necktie as desired.

2. Description of the Related Art

A necktie is one type of clothing frequently used by modern persons. When wearing a necktie, one positions the necktie in the collar of a shirt and then makes a knot near the neck.

However, this type of necktie requires much time and effort to wear since a user must make a knot whenever user wears the necktie. In addition, if the length of the worn necktie is not appropriate, wearer must go through the cumbersome process of untying and retying the necktie.

Recently, there is provided a necktie, which has a clip at the knot portion so that the necktie can be united to the neck portion of a shirt without making a knot.

This necktie with a clip is easy and convenient to wear, but its knot may become crooked or easily separated from the shirt during wearing. In addition, it is impossible to adjust the length of the necktie, so wearer must purchase another necktie specifically suitable for wearer's figure. In addition, each necktie provides only one knot shape with one design, so the wearer may grow tired of the necktie and tend not to wear it.

In order to solve such problems, the present invention proposes a technique, as discussed in Korean Utility Model Registration No. 246000, in which a roller is mounted in a knot shape in a wearing device for a necktie, and a clip for affixing the necktie to a shirt is mounted on the back side of the wearing device. By sliding the necktie on the roller, a wearer may adjust the length of the necktie; thus, a wearer may put on the necktie with little effort. In addition, by improvement of a combining force, the wearing device may prevent the knot from becoming crooked and the necktie from becoming separated from the shirt. Furthermore, the length of the necktie may be adjusted, and various neckties may be worn at various times, using only one wearing device.

However, the conventional necktie-wearing device has some problems. It has a relatively complicated configuration for installing the roller in the wearing device, and expensive to manufacturing. Since the rear surface of the roller and the wearing device is formed flat for smooth operation of the rollers, it provides an aesthetically unpleasing appearance whereby both sides of the wearing device are separated from the human body.

SUMMARY OF THE INVENTION

To solve the aforementioned problems, the present invention introduces a new necktie wearing device which provides a better appearance by making the device in such a way that it may be worn closer to the human body; reduces the manufacturing cost by simplifying its configuration; and is easy to use because of the provision of a lifting plate for moving the necktie up and down, a magnetic support plate for affixing the necktie to a shirt, and a knot unit having a knot shape for inserting the support plate therein.

In one embodiment of the present invention, there is provided a necktie wearing device including a support plate having a curved shape corresponding to the front surface of the necktie knot; a magnet mounted in the center of the support plate; a rod-shaped lifting plate connected to both ends of the support plate by use of strings; a case provided on one side of the support plate, which case has a magnet therein; and a knot unit made of a fiber and having a necktie knot shape, the knot unit including a space for insertion of the support plate and a necktie drawing hole formed at the lower end thereof.

Preferably, a fixing cover having a fixing pin at the inner center is hinged to the back surface of the case, and a hole is formed at the center of the magnet and the case so that the fixing pin is capable of being detachably inserted into the hole.

BRIEF DESCRIPTION OF THE DRAWINGS

The above objects, features and advantages of the present invention will become more apparent from the following detailed description when taken in conjunction with the accompanying drawings, in which.

DESCRIPTION OF THE PREFERRED EMBODIMENT

Figure 1:
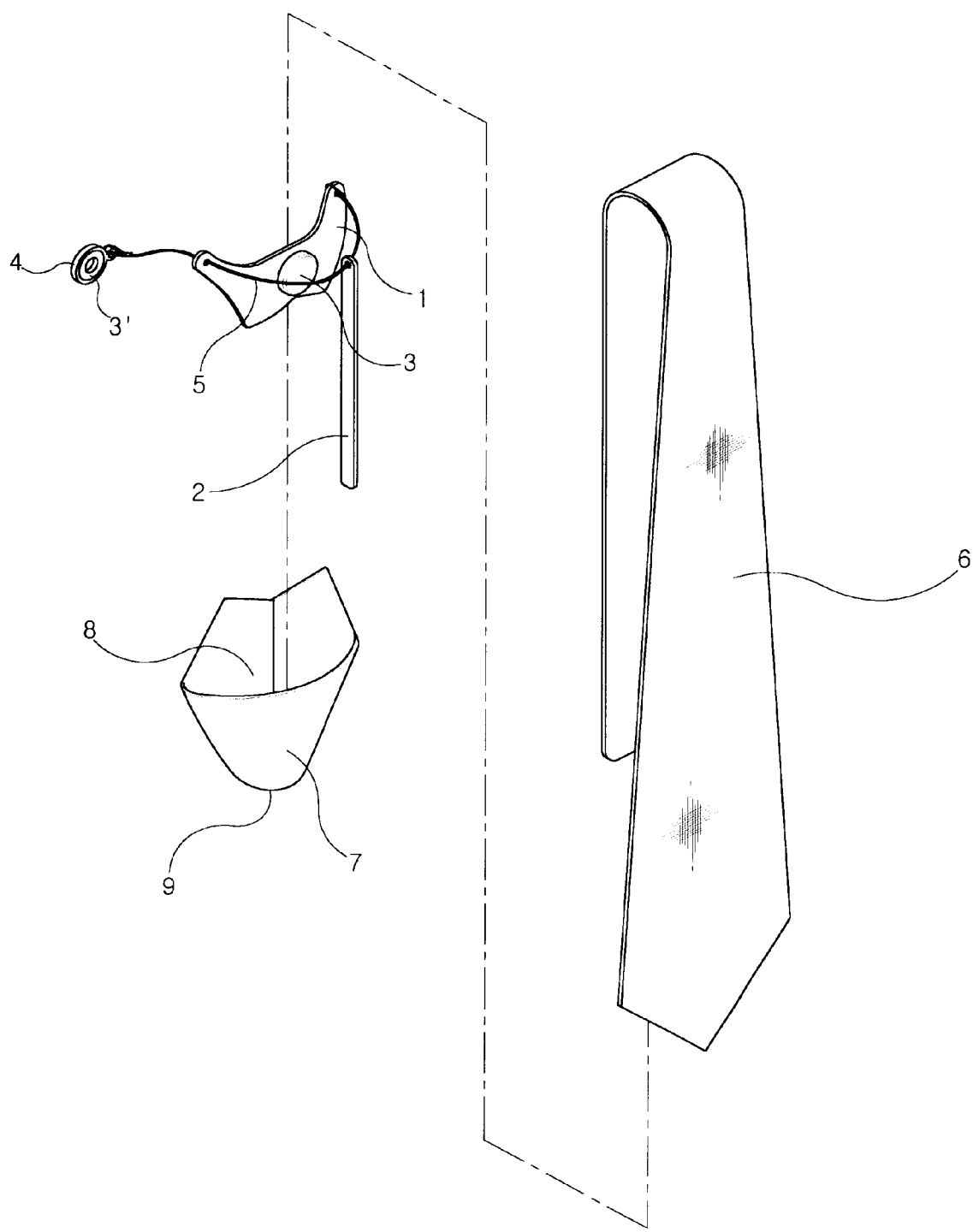
FIG. 1 is an exploded perspective view showing a necktie-wearing device according to the preferred embodiment of the present invention.

Hereinafter, the present invention will be described in more detail referring to the drawings.

Referring to FIG. 1, the necktie-wearing device includes a support plate 1 having a curved shape corresponding to the front surface of a necktie knot. A magnet 3 is mounted in the center of the support plate 1. In addition, a rod-shaped lifting plate 2 is connected to both ends of the support plate 1 by use of strings 5. The device also includes a case 4 provided on one side of the support plate 1. The case 4 has a magnet 3 therein. The device also separately includes a knot unit 7 made of a fiber. The knot unit 7 has a necktie knot shape in which an insert space 8 is formed in the knot unit 7 so that the support plate 1 may be inserted therein. In addition, a necktie-drawing hole 9 is formed at the lower end of the knot unit 7.

Figure 6:
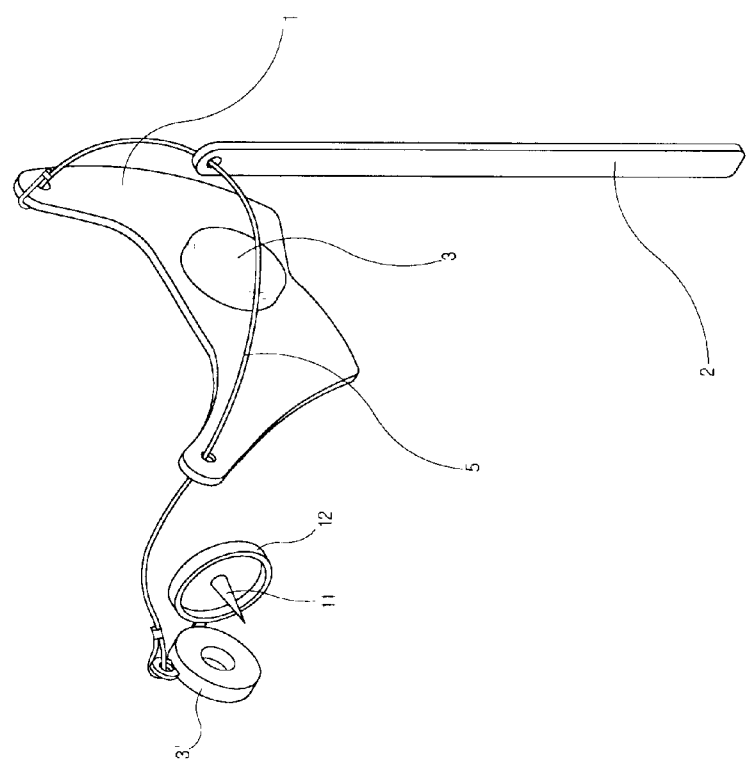
FIG. 6 is a perspective view showing the necktie-wearing device, which is provided with a fixing pin according to another embodiment of the present invention.

As shown in FIG. 6, a fixing cover 12 having a fixing pin 11 at the inner center can be hinged to the rear surface of the case 4. Also, a hole can be formed at the center of the magnet 3 and the case 4 so that the fixing pin 11 is capable of being detachably inserted into the hole.

Now the operation of the necktie-wearing device according to the present invention is described.

Figure 3:
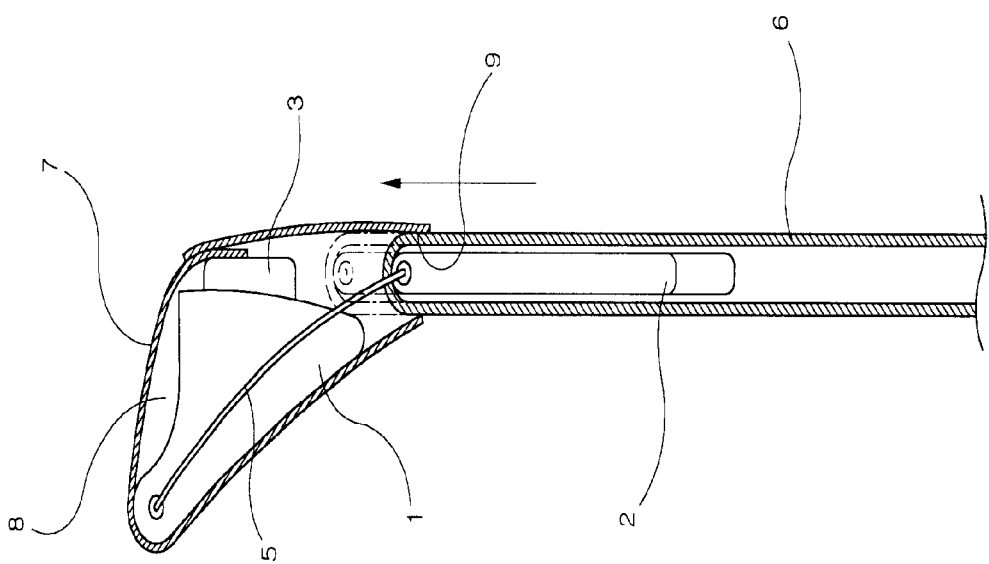
FIG. 3 is a side sectional view showing the necktie-wearing device in which a necktie is held to the support plate and inserted into the knot unit.
Figure 2:
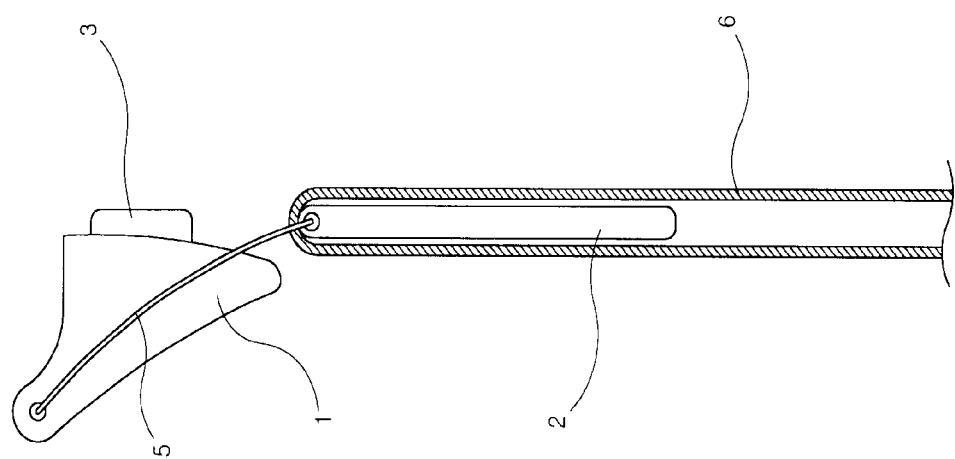
FIG. 2 is a side view showing the necktie-wearing device in which a necktie is hung on a support plate.
Figure 4:
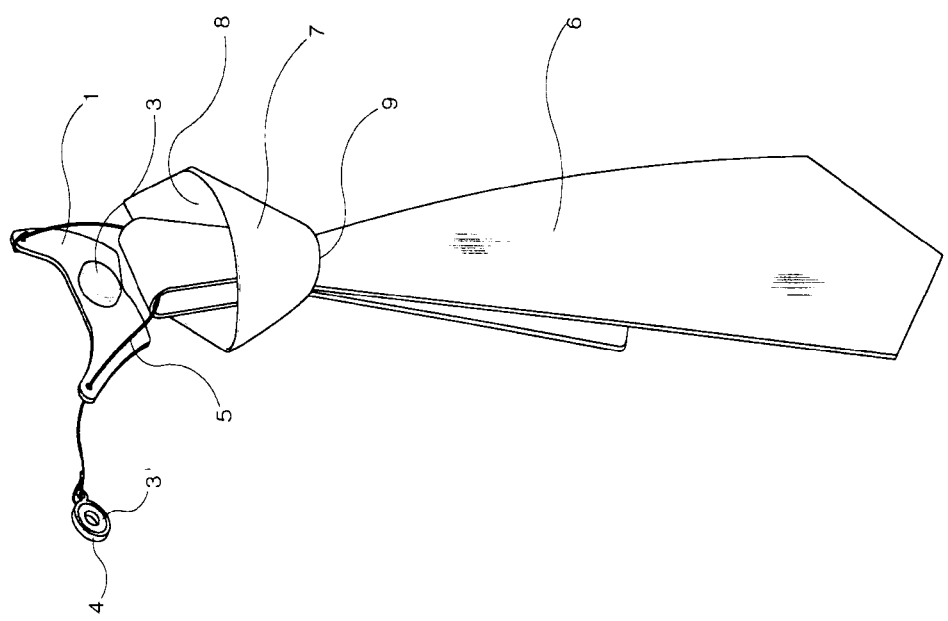
FIG. 4 is a perspective view showing the necktie-wearing device in which a necktie is held to the support plate and inserted into a knot unit.

When using the necktie wearing device of the present invention, a necktie is at first hung from the strings 5 connected to both ends of the support plate 1 so that the lifting plate 2 is positioned in the folded necktie, as shown in FIG. 2. Then, the necktie 6 is inserted into the knot unit 7 so that the necktie is drawn through the hole 9 formed at the lower end of the knot unit 7, and the support plate 1 is inserted into the space 8 of the knot unit 7, as shown in FIGS. 3 and 4.

Figure 5:
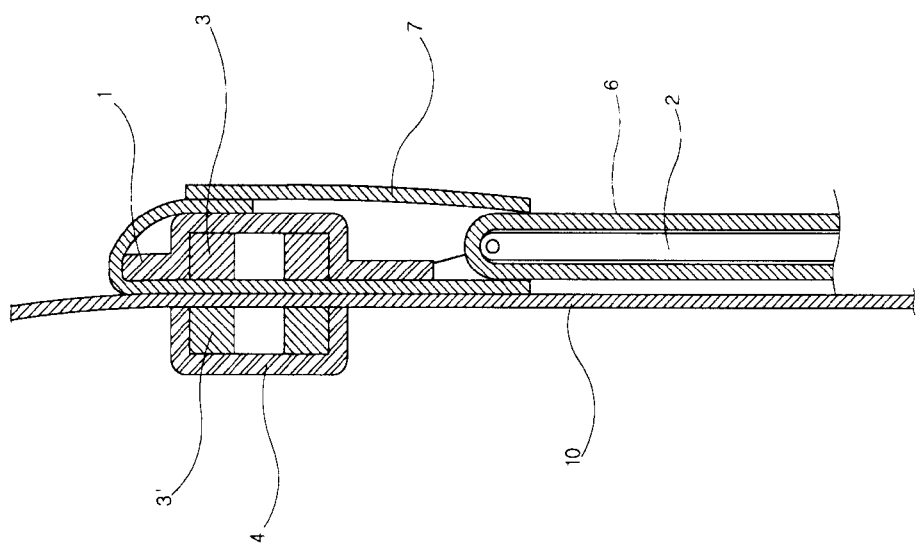
FIG. 5 is a sectional view showing the necktie-wearing device, which is affixed to a shirt.

After affixing the necktie 6 to the knot unit 7 by use of the support plate 1 as described above, the case 4 protruded to one side of the knot unit 7 is positioned inside the shirt 10 at the installation point of the magnet 3 on the support plate 1, as shown in FIG. 5. Thus, the magnet 3 of the case 4 and the support plate 1 are attached to each other by a magnetic force and thereby are affixed to the shirt 10.

To adjust the length of the necktie 6 described above, a wearer grasps the necktie 6 and lifts the plate 2 inside of the necktie 6, drawing it through the drawing hole 9 of the knot unit 7 by the fingers. Then, the wearer draws the necktie 6 from the drawing hole 9 further in order to adjust the length of the necktie as desired.

Figure 7:
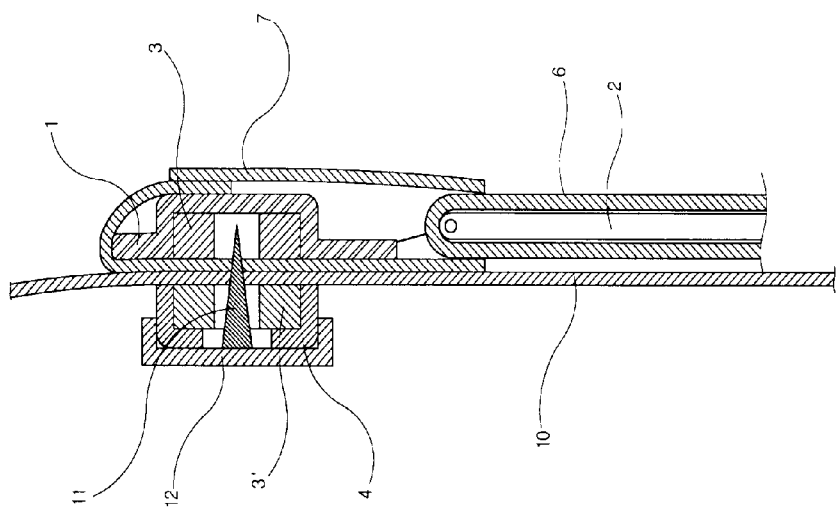
FIG. 7 is a sectional view showing the necktie-wearing device of FIG. 6, which is affixed to a shirt by use of the fixing pin.

Referring to FIG. 6, the fixing pin 11 is mounted to the back surface of the case 4. The fixing pin 11 is fixed through the shirt 10 as shown in FIG. 7, so it may prevent the necktie from slipping down during its wearing.

In addition, since the support plate 1 has a curved shape corresponding to a shape of the front surface of the necktie knot, the necktie can be worn closer to the human body, which improves the wearing comfort of the necktie and provides for a better appearance.

The necktie-wearing device according to the present invention has a lift plate for moving the necktie up and down, a support plate having a magnet for affixing the necktie to a shirt, and a knot unit having a necktie knot shape for insertion of the support plate. Additionally, the necktie wearing device of the present invention may improve the wearing comfort of a necktie, as well as provide for a better appearance a simpler configuration, a lower manufacturing cost and convenience to the wearer.

What is claimed is:

1. A necktie wearing device comprising:

a support plate having a curved shape corresponding to front surface of necktie knot, a magnet mounted in the center of said support plate, a rod-shaped lifting plate connected to the support plate by using strings connected to both ends of said support plate, a case provided on one side of the support plate having a magnet therein, a knot unit made of a fiber and having a necktie knot shape, said knot unit including a space for insertion of said support plate, and a necktie drawing hole being formed at lower end thereof.

2. The necktie wearing device according to claim 1, wherein a fixing cover (12) having a fixing pin (11) at inner center is hinged to back surface of case (4), and a hole is formed at the center of magnet (3) and the case (4) so that the fixing pin (11) is capable of being detachably inserted into the hole.

* * * * *